(12) United States Patent
Krolik et al.

(10) Patent No.: US 6,663,651 B2
(45) Date of Patent: Dec. 16, 2003

(54) SYSTEMS AND METHODS FOR VASCULAR FILTER RETRIEVAL

(75) Inventors: Jeff A. Krolik, Campbell, CA (US); Amr Salahieh, Campbell, CA (US); Jackson F. Demond, Santa Cruz, CA (US); Farhad Khosravi, San Mateo, CA (US)

(73) Assignee: Incept LLC, San Mateo, CA (US)

( * ) Notice: Subject to any disclaimer, the term of this patent is extended or adjusted under 35 U.S.C. 154(b) by 381 days.

(21) Appl. No.: 09/764,732

(22) Filed: Jan. 16, 2001

(65) Prior Publication Data

US 2002/0095170 A1 Jul. 18, 2002

(51) Int. Cl.$^7$ .............................................. A61M 29/00
(52) U.S. Cl. ...................................... 606/200; 128/899
(58) Field of Search ........................... 606/1, 108, 198, 606/200; 128/899

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |
| 4,662,885 A | 5/1987 | DiPisa, Jr. | |
| 4,705,517 A | 11/1987 | DiPisa, Jr. | |
| 4,706,671 A | 11/1987 | Weinrib | |
| 4,723,549 A | 2/1988 | Wholey et al. | |
| 4,728,319 A | 3/1988 | Masch | |
| 4,733,665 A | 3/1988 | Palmaz | |
| 4,790,812 A | 12/1988 | Hawkins, Jr. et al. | |

(List continued on next page.)

FOREIGN PATENT DOCUMENTS

| | | |
|---|---|---|
| DE | 28 21 048 | 7/1980 |
| DE | 34 17 738 | 11/1985 |

(List continued on next page.)

OTHER PUBLICATIONS

US 3,686,904, 8/1972, Forster (withdrawn)
"Atherosclerotic Disease of the Aortic Arch as a Risk Factor of Recurrent Ischemic Stroke," *The New England Journal of Medicine*, pp. 1216–1221 (May 1996).

(List continued on next page.)

*Primary Examiner*—Gloria M. Hale
(74) *Attorney, Agent, or Firm*—Crompton, Seager & Tufte LLC

(57) ABSTRACT

Apparatus and methods for retrieving a vascular filter from a vessel are provided wherein a retrieval adapter is delivered to a treatment site concurrently along with an interventional device to reduce the number of steps required to remove the vascular filter. The retrieval adapter also reduces the possibility of entangling the vascular filter with a stent disposed within the vessel during removal of the vascular filter. A separate retrieval catheter is also described for use in conjunction with the retrieval adapter.

30 Claims, 6 Drawing Sheets

U.S. PATENT DOCUMENTS

| | | | |
|---|---|---|---|
| 4,790,813 A | 12/1988 | Kensey | |
| 4,794,928 A | 1/1989 | Kletschka | |
| 4,794,931 A | 1/1989 | Yock | |
| 4,800,882 A | 1/1989 | Gianturco | |
| 4,807,626 A | 2/1989 | McGirr | |
| 4,842,579 A | 6/1989 | Shiber | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,898,575 A | 2/1990 | Fischell et al. | |
| 4,907,336 A | 3/1990 | Gianturco | |
| 4,921,478 A | 5/1990 | Solano et al. | |
| 4,921,484 A | 5/1990 | Hillstead | |
| 4,926,858 A | 5/1990 | Gifford, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,126 A | 8/1991 | Gianturco | |
| 5,053,008 A | 10/1991 | Bajaj | |
| 5,053,044 A | 10/1991 | Mueller et al. | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,100,423 A | 3/1992 | Fearnot | |
| 5,100,424 A | 3/1992 | Jang et al. | |
| 5,100,425 A | 3/1992 | Fischell et al. | |
| 5,102,415 A | 4/1992 | Guenther et al. | |
| 5,104,399 A | 4/1992 | Lazarus | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,190,546 A | 3/1993 | Jervis | |
| 5,195,955 A | 3/1993 | Don Michael | |
| 5,224,953 A | 7/1993 | Morgentaler | |
| 5,306,286 A | 4/1994 | Stack et al. | |
| 5,314,444 A | 5/1994 | Gianturco | |
| 5,314,472 A | 5/1994 | Fontaine | |
| 5,318,576 A | 6/1994 | Plassche, Jr. et al. | |
| 5,329,942 A | 7/1994 | Gunther et al. | |
| 5,330,484 A | 7/1994 | Gunther et al. | |
| 5,330,500 A | 7/1994 | Song | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,366,464 A | 11/1994 | Belknap | |
| 5,366,473 A | 11/1994 | Winston et al. | |
| 5,370,657 A | 12/1994 | Irie | |
| 5,370,683 A | 12/1994 | Fontaine | |
| 5,376,100 A | 12/1994 | Lefebvre | |
| 5,383,887 A | 1/1995 | Nadal | |
| 5,383,892 A | 1/1995 | Cardon et al. | |
| 5,383,926 A | 1/1995 | Lock et al. | |
| 5,387,235 A | 2/1995 | Chuter | |
| 5,395,349 A | 3/1995 | Quiachon et al. | |
| 5,397,345 A | 3/1995 | Lazerus | |
| 5,405,377 A | 4/1995 | Cragg | |
| 5,409,454 A | 4/1995 | Fischell et al. | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,423,885 A | 6/1995 | Williams | |
| 5,425,765 A | 6/1995 | Tiefenbrun et al. | |
| 5,443,498 A | 8/1995 | Fontaine | |
| 5,449,372 A | 9/1995 | Schmaltz et al. | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A | 8/1996 | Miller et al. | |
| 5,562,724 A | 10/1996 | Vorwerk et al. | |
| 5,569,274 A | 10/1996 | Rapacki et al. | |
| 5,569,275 A | 10/1996 | Kotula et al. | |
| 5,634,897 A | 6/1997 | Dance et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,746,758 A | 5/1998 | Nordgren et al. | |
| 5,749,848 A | 5/1998 | Jang et al. | |
| 5,769,816 A | 6/1998 | Barbut et al. | |
| 5,779,716 A | 7/1998 | Cano et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,817,102 A | 10/1998 | Johnson et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,893,867 A | 4/1999 | Bagaoisan et al. | |
| 5,895,399 A | 4/1999 | Barbut et al. | |
| 5,902,263 A | 5/1999 | Patterson et al. | |
| 5,906,618 A | 5/1999 | Larson, III | |
| 5,908,435 A | 6/1999 | Samuels | |
| 5,910,154 A * | 6/1999 | Tsugita et al. | 606/200 |
| 5,911,734 A | 6/1999 | Tsugita et al. | |
| 5,916,193 A | 6/1999 | Stevens et al. | |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |
| 5,928,203 A | 7/1999 | Davey et al. | |
| 5,928,218 A | 7/1999 | Gelbfish | |
| 5,934,284 A | 8/1999 | Plaia et al. | |
| 5,935,139 A | 8/1999 | Bates | |
| 5,938,645 A | 8/1999 | Gordon | |
| 5,941,869 A | 8/1999 | Patterson et al. | |
| 5,941,896 A | 8/1999 | Kerr | |
| 5,947,995 A | 9/1999 | Samuels | |

| | | | |
|---|---|---|---|
| 5,951,585 A | 9/1999 | Cathcart et al. | |
| 5,954,745 A | 9/1999 | Gertler et al. | |
| 5,976,172 A | 11/1999 | Homsma et al. | |
| 5,989,210 A | 11/1999 | Morris et al. | |
| 5,989,271 A | 11/1999 | Bonnette et al. | |
| 5,989,281 A | * 11/1999 | Barbut et al. | 606/200 |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,051,014 A | 4/2000 | Jang | |
| 6,053,932 A | 4/2000 | Daniel et al. | |
| 6,059,814 A | 5/2000 | Ladd | |
| 6,068,645 A | 5/2000 | Tu | |
| 6,086,605 A | 7/2000 | Barbut et al. | |
| 6,129,739 A | 10/2000 | Khosravi | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,214,026 B1 | 4/2001 | Lepak et al. | |
| 6,217,600 B1 | 4/2001 | DiMatteo | |
| 2002/0042626 A1 | 4/2002 | Hanson et al. | |

FOREIGN PATENT DOCUMENTS

| | | |
|---|---|---|
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 179 321 A2 | 2/2002 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 00/49970 | 8/0000 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 09/34729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/16845 | 3/2000 |
| WO | WO 01/12082 A1 | 2/2001 |

OTHER PUBLICATIONS

"Endovascular Grafts, Stents Drive Interventional Radiology Growth," *Cardiovascular Device Update*, 2(3):1–12 (Mar. 1996).

"Protruding Atheromas in the Thoracic Aortic and Systemic Embolization ," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601–604 (Sep. 1983).

Cragg, Andrew et al., "Nonsurgical Placement of Arterial Endoprosthesis: A New Technique Using Nitinol Wire," *AJR*, pp. 261–263 (Apr. 1983).

Diethrich et al., "Percutaneous Techniques for Endoluminal Carotid Interventions," *J. Endovasc. Surg.*, 3:182–202 (1996).

Fadali, A. Moneim, "A filtering device for the prevention of particulate embolization during the course of cardiac surgery," *Surgey*, 64(3):634–639 (Sep. 1968).

Haissaguerre et al., "Spontaneous Initiation of Atrial Fibrillation by Ectopic Beats Originating in the Pulmonary Veins," *The New England Journal of Medicine*, 339(10):659–666 (Sep. 1988).

Jordan, Jr. et al., "Microemboli Detected by Transcranial Doppler Monitoiring . . . ," *Cardiovascular Surgery*, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Ballon Dilation: an Experimental Study," *Laboratory Investigation*, 69(4):772–774 (Apr. 1984).

Marache et al., "Percutaneous Transluminal Venous Angioplasty . . .," *American Heart Journal,* 125(2 Pt 1):362–366 (Feb. 1993).

Mazur et al., "Directional Atherectomy with the Ominicath™: A Unique New Catheter System," *Catheterization and Cardiovascular Diagnosis*, 31:17–84 (1994).

Moussa, MD, Issaam "Stents Don't Require Systemic Anticoagulation . . . But the Technique (and Results) Must be Optimal," *Journal of Invasive Cardiol.*, 8(E):3E–7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386–392 (1998).

Theron et al., "New Triple Coaxial Catheter System for Carotid Angioplasty with Cerebral Protection," *American Journal of Neuroradiology*, 11:869–874 (1990).

Tunick et al., "Protruding atherosclerotic plaque in the aortic archo f patients with systemic embolization: A new finding seen by transesophageal echocardiography," *American Heart Journal* 120(3):658–660 (Sep. 1990).

Waksman et al., "Distal Embolization is Common After Directional Atherectomy . . .," *American Heart Journal*, 129(3):430–435 (1995).

Wholey, Mark H. et al., PTA and Stents in the Treatment of Extracranial Circulation, *The Journal of Invasive Cardiology*, 8(E):25E–30E (1996).

\* cited by examiner

SYSTEMS AND METHODS FOR VASCULAR FILTER RETRIEVAL

FIELD OF THE INVENTION

The present invention relates to apparatus and methods for retrieving a vascular device, such as a filter, from within a vessel. More particularly, the present invention provides apparatus useful for retrieving a vascular filter used to prevent embolization associated with diagnostic or therapeutic interventional procedures, thrombectomy and embolectomy.

BACKGROUND OF THE INVENTION

Percutaneous interventional procedures to treat occlusive vascular disease, such as angioplasty, atherectomy, and stenting, often dislodge material from the vessel walls. This dislodged material, known as emboli, enters the bloodstream and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, involves the introduction of foreign objects into the bloodstream, and also may result in the formation of clots or release of emboli. Such particulate matter, if released into the bloodstream, also may cause infarction or stroke.

Numerous blood filters are known that are designed to capture material liberated from vessel walls during the treatment of vascular disease. Such treatment procedures, such as angioplasty, atherectomy and stenting, typically involve transluminally inserting an interventional device to the treatment site along a guidewire. Upon completion of the procedure, the interventional device is removed from the patient's blood vessel, and a retrieval mechanism, such as a sheath, is advanced along the guidewire in order to retrieve the blood filter.

One drawback associated with using a sheath to retrieve a filter is that the retrieval process requires two steps: (1) the interventional device (e.g., angioplasty catheter) must be removed and (2) the retrieval sheath must then be advanced along the guidewire to retrieve the filter. This additional exchange adds time to the length of the procedure, involves introduction of an additional element (the retrieval catheter) into the patient's vasculature, and enhances the risk of dislodging the filter and permitting emboli to escape therefrom.

Moreover, as the retrieval sheath is advanced along the guidewire, its distal end may become entangled with a stent disposed within the patient's vessel. If, for example, a stent has been deployed, the distal end of the retrieval sheath may inadvertently engage a stent strut, preventing further advancement of the retrieval sheath within the vessel, or even possibly causing vessel dissection.

One disadvantage associated with attempting to retrieve a vascular filter using the guidewire lumen of an interventional device, such as an angioplasty catheter, is that the diameters of such lumens are typically quite small, e.g., 0.014 inch. Accordingly, it is not possible to retrieve previously known vascular filters using the guidewire lumens of most interventional devices.

In view of the foregoing, it would be desirable to provide improved apparatus and methods that streamline retrieval of a vascular filter.

It further would be desirable to provide improved apparatus and methods that facilitate retrieval of a vascular filter, with reduced risk of entangling a retrieval sheath in a deployed stent.

SUMMARY OF THE INVENTION

In view of the foregoing, it is an object of the present invention to provide improved apparatus and methods that streamline retrieval of a vascular filter.

It is another object of the present invention to provide improved apparatus and methods that facilitate retrieval of a vascular filter, with reduced risk of entangling a retrieval sheath in a deployed stent.

These and other objects of the present invention are accomplished by providing a retrieval apparatus that reduces the time and effort required to retrieve a vascular filter from a patient's vessel.

In one preferred embodiment, the present invention includes a retrieval adapter having a proximal end configured to be fitted to the end of an interventional device, such as an angioplasty catheter, and a radially expandable distal end. Upon completion of an interventional procedure such as angioplasty, the balloon of the angioplasty catheter is deflated and the angioplasty catheter then is advanced along the guidewire until the adapter captures the vascular filter.

Alternatively, upon completion of the interventional procedure, the guidewire and attached vascular filter may be withdrawn proximally until the vascular filter engages and is caused to be collapsed by the adapter. Once the vascular filter is collapsed, the vascular filter is partially withdrawn within the adapter, and the vascular filter, adapter, interventional device and guidewire are all removed from the vessel. This streamlined procedure provides a substantial improvement over previously known systems, which typically require exchanging the interventional device for a retrieval sheath before retrieving the vascular filter from the treatment site.

In another embodiment, the retrieval adapter of the present invention may be loaded directly onto the guidewire having the vascular filter so that the adapter is delivered to a treatment site concurrently with the filter. After completion of a diagnostic or therapeutic procedure involving an interventional device, such as an angioplasty catheter, the interventional device is advanced along the guidewire. As the distal end of the interventional device moves distally, it abuts against the adapter and urges the adapter into contact with the filter, thereby causing the adapter to collapse and capture the vascular filter. Alternatively, as for the previous embodiment, the interventional device may be held stationary and the vascular filter and adapter retracted proximally.

In yet another embodiment, the present invention includes a retrieval catheter having proximal and distal ends. The proximal end of the catheter is loaded onto the distal end of an interventional device, and that assemblage then is loaded onto the guidewire having the vascular filter. After completion of a diagnostic or therapeutic procedure, such as stent deployment, the retrieval catheter is advanced over the working element of the interventional device (e.g., the deflated balloon) and the vascular filter. Alternatively, the retrieval catheter may be held stationary and the vascular filter and guidewire retracted proximally to collapse and capture the filter in the retrieval sheath.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

The present invention is directed to apparatus and methods for closing the mouth of a vascular filter or similar vascular device so as to prevent emboli from escaping during contraction and removal of the vascular filter or device, while reducing the number of equipment exchanges associated with such removal.

A number of vascular filters are known for providing distal protection against embolization in conjunction with a transluminal diagnostic or therapeutic procedure, such as angioplasty. These filters generally are deployed distal to a vascular lesion prior to undertaking a diagnostic or therapeutic procedure, and are designed to filter emboli liberated during the procedure from the patient's blood. A brief description of a number of these filters is provided as context for advantages achievable using the apparatus of the present invention.

Figure 1:
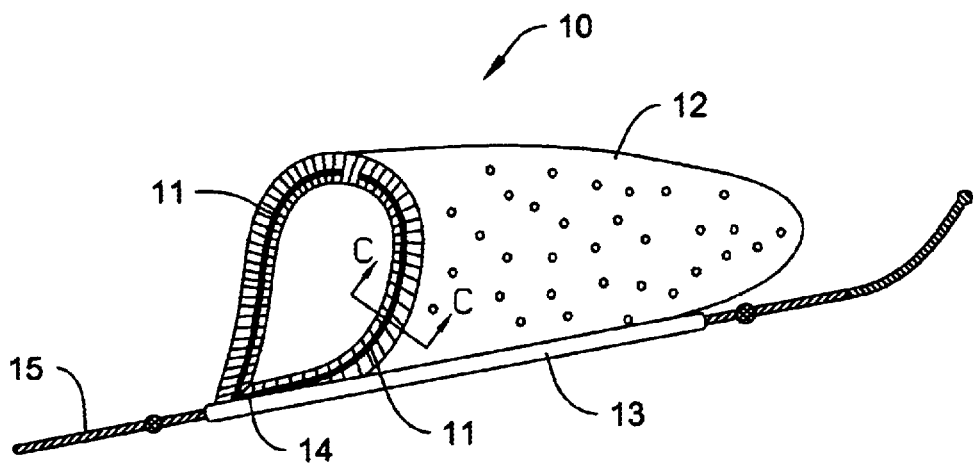
FIG. 1 is a perspective view of a first previously known vascular filter suitable for use with the apparatus of the present invention.

FIG. 1 shows vascular filter 10 described in U.S. Pat. No. 6,129,739 to Khosravi et al., which is incorporated herein in its entirety. Vascular filter 10 includes articulated support hoop 11 carrying blood permeable sac 12. Support hoop 11 is attached to tube 13 at point 14, and permits guidewire 15 to be rotated independently of support hoop 11. Blood permeable sac 12 filters emboli and other undesirable material from blood passing through the filter, while permitting blood cells to pass freely therethrough. When an interventional procedure, e.g., angioplasty or stenting, is completed, vascular filter 10 is retrieved by partially withdrawing support hoop 11 into the lumen of the interventional device (e.g., angioplasty catheter), and removing the catheter and vascular filter.

Figure 2:
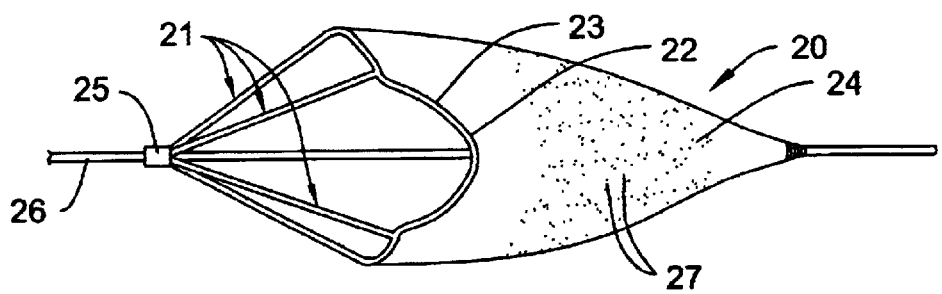
FIG. 2 is a perspective view of another previously known vascular filter suitable for use with the apparatus of the present invention.

FIG. 2 depicts another type of vascular filter suitable for use with the methods and apparatus of the present invention, and is described in U.S. Pat. No. 6,152,946 to Broome et al., which is incorporated herein by reference. Vascular filter 20 includes a plurality of longitudinally-extending ribs 21 forming frame 22 that supports mouth 23. Cone-shaped filter 24 is coupled to mouth 23. Ribs 21 are coupled to collar 25, which is displaced distally along guidewire 26 to expand and deploy frame 22 and filter 24. Filter 24 includes holes 27 that permit blood to pass through the filter, while trapping emboli. Vascular filter 20 is collapsed for retrieval by applying a load against ribs 21 that causes collar 25 to slide proximally, thereby closing the vascular filter.

Figure 3:
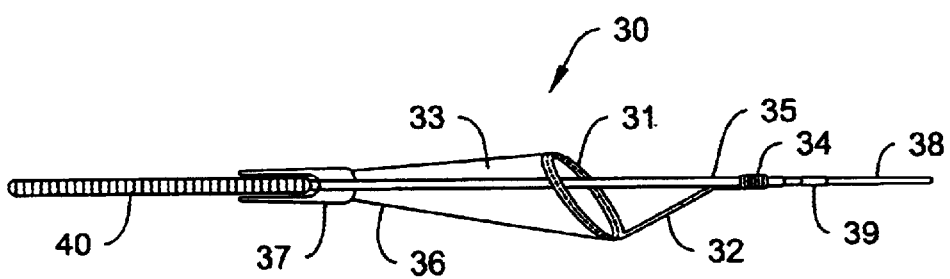
FIG. 3 is a side view of yet another vascular filter suitable for use with the apparatus of the present invention.

Referring now to FIG. 3, another vascular filter suitable for use with the apparatus and methods of the present invention is described. Vascular filter 30 is described in detail in U.S. patent application Ser. No. 09/764,774, filed Jan. 16, 2001 (now abandoned), and is summarily described here.

Vascular filter 30 preferably includes self-expanding support hoop 31 mounted on suspension strut 32, and supports blood permeable sac 33. Blood permeable sac 33 comprises a biocompatible polymeric material having a multiplicity of pores. Suspension strut 32 is affixed at proximal end 34 to tube 35, and positions support hoop 31 approximately concentric to tube 35 when disposed in a substantially straight length of vessel, but advantageously permits the support hoop to become eccentrically displaced relative to support tube 35 when the filter is deployed in a curved vessel.

Distal end 36 of blood permeable sac 33 is illustratively mounted to nose cone 37, which is in turn mounted to tube 35. Filter 30 is mounted on guidewire 38 between proximal stop 39 and enlarged floppy tip 40 of the guidewire, which functions as a distal stop. Tube 35 permits guidewire 38 to rotate independently of filter 30, thereby permitting floppy tip 40 of the guidewire to be directed within the vessel without causing the blood permeable sac to become wrapped around guidewire 38.

Figure 4A:
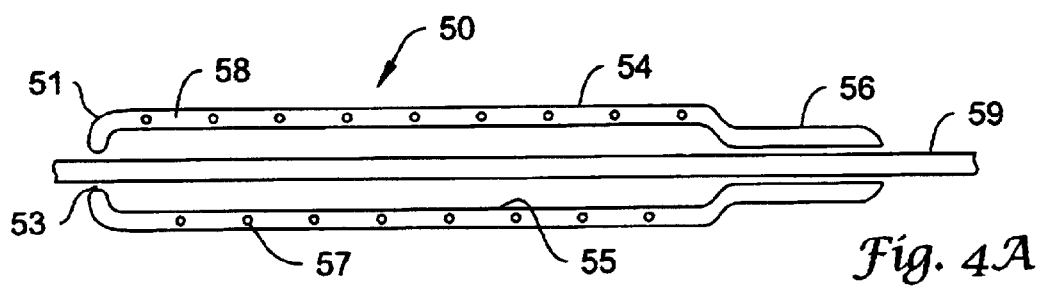
FIGS. 4A and 4B are, respectively, side sectional and side views of apparatus of the present invention.
Figure 4B:
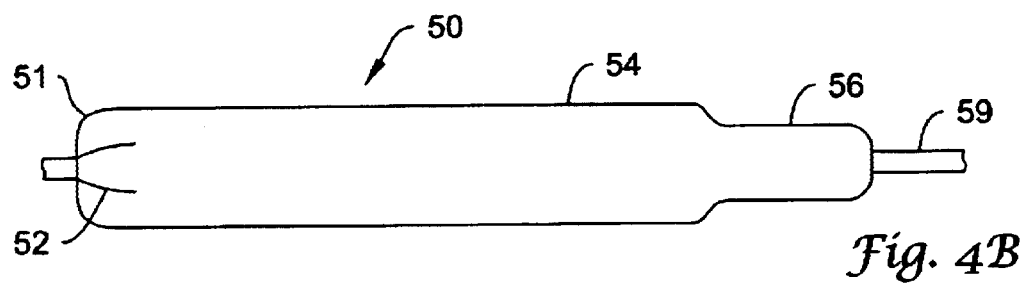

Referring now to FIGS. 4A and 4B, apparatus constructed in accordance with the principles of the present invention is described. Apparatus 50 of the present invention, referred to hereinafter as a "retrieval adapter," permits a conventional interventional device, such as an angioplasty catheter or stent delivery system, to be employed in retrieving a vascular filter of the types shown in FIGS. 1–3.

Adapter 50 preferably includes curved distal end 51 having expansion slits 52, opening 53, tubular body 54 having internal lumen 55, and tapered proximal region 56. Optionally, adapter 50 may include helical coil 57 embedded in wall 58 to reinforce the adapter. Adapter 50 preferably is constructed of a thin biocompatible material, such as polyethylene, polypropylene, polyurethane, polyester, polyethylene terephthalate, nylon, polytetrafluoroethylene, or Pebax®, however, any other suitable biocompatible material or a combination of such materials may be used, if desired.

Adapter 50 preferably is constructed so that it has sufficient stiffness to be urged along guidewire 59 and through curved vasculature within a patient's circulatory system. Tapered proximal region 56 enables adapter 50 to be coupled to a conventional interventional device, such as an angioplasty catheter or stent delivery catheter. Adapter 50 has sufficient stiffness so as to not buckle or kink when being urged into engagement with a previously deployed vascular filter during filter retrieval.

Distal end 51 preferably has a smooth, rounded tip to reduce the risk of adapter 50 from catching a flap of dissected tissue or on a stent deployed within a vessel. Expansion slits 52 permit the curved portions of distal end 51 to expand to accept a vascular filter when adapter 50 is advanced along guidewire 59, so that opening 53 at least partially accommodates a portion of a deployed vascular filter. Adapter 50 optionally may comprise a radiopaque material, e.g., a barium sulfate-infused ($BaSO_4$) polymer or by using metal markers, to permit viewing of the adapter using a fluoroscope. In addition, coil 57 also may comprise a radiopaque material.

Tapered region 56 is configured so that it engages the interior or exterior surface of a conventional interventional device, such as an angioplasty catheter or stent delivery system. Tapered region 56 also aids in disposing adapter 50 concentric with respect to guidewire 59. In accordance with the principles of the present invention, adapter 50 is delivered at the same time as an interventional device to be used for the diagnostic or therapeutic treatment. Accordingly, adapter 50 provides a significant improvement over previously known filter retrieval systems, by eliminating the need for a separate catheter exchange to retrieve the vascular filter.

Optionally, adapter 50 may be bonded to the distal end of the interventional device using a standard biocompatible adhesive, press fitting, or other suitable means. For example, the internal surface of lumen 55 at tapered proximal end 56 may be coated with a pressure-sensitive adhesive. A clinician may then couple adapter 50 to the distal end of an interventional device and apply pressure to fix the adapter to the device. The adapter then is delivered with the interventional device, and upon completion of the diagnostic or therapeutic procedure, is used to retrieve the vascular filter. Alternatively, adapter 50 may be provided in a kit including a vascular filter mounted on a guidewire (not shown).

Figure 5A:
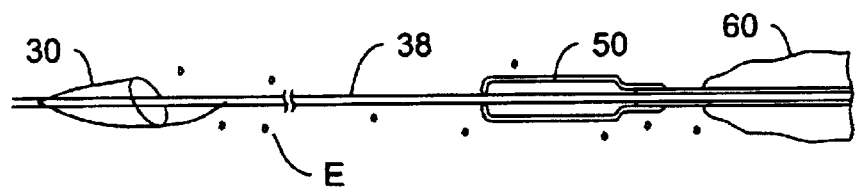
FIGS. 5A and 5B are side sectional views illustrating the use of the apparatus of FIG. 4 to retrieve the vascular filter of FIG. 3.
Figure 5B:
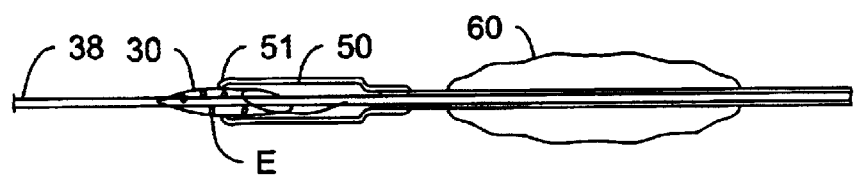

Referring now to FIGS. 5A and 5B, a method of employing the adapter of FIG. 4 to recover a vascular filter is described. In FIG. 5A, vascular filter 30 of FIG. 3 is shown deployed along guidewire 38. After insertion of guidewire 38 and deployment of vascular filter 30, adapter 50 is mounted to the distal end of an interventional device 60, illustratively and angioplasty catheter 60. Adapter 50 and angioplasty catheter 60 then are advanced along guidewire 38 to a location just proximal of, or in contact with, the vascular filter, where angioplasty catheter 60 is used to treat vascular disease. Inflation of the balloon of angioplasty catheter 60 causes emboli E to be liberated from the lesion, and be carried by the blood flow into filter 30.

With respect to FIG. 5B, after the interventional procedure is completed, the balloon of angioplasty catheter 60 is deflated and catheter 60 is advanced distally along guidewire 38 to bring adapter 50 into contact with filter 30. Filter 30 preferably is received within distal end 51 of adapter 50 when the adapter is advanced further in the distal direction. Alternatively, adapter 50 may receive at least a portion of filter 30 by retracting guidewire 38 proximally while holding angioplasty catheter 60 and adapter 50 stationary.

The degree to which vascular filter 30 is enclosed within adapter 50 may be varied depending on treatment requirements. This may be accomplished by altering the size of adapter 50 or by controlling the movement of catheter 60 along guidewire 38. For example, in some cases it may be sufficient to enclose the mouth of filter 30 within adapter 50 to facilitate retrieval. In such a situation, adapter 50 may be constructed so that it is somewhat smaller than the length of filter 30, so only the mouth of the device fits into the adapter. In other situations, however, it may be desired to enclose some or all of filter 30 within adapter 50, and in such a case adapter 50 may be constructed so that it is somewhat larger than the length of vascular filter 30.

Figure 6:
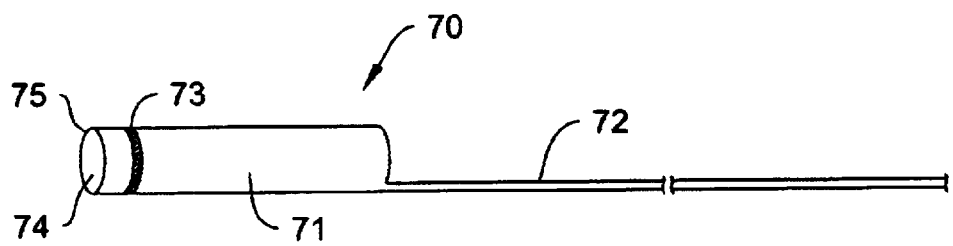
FIG. 6 is a side view of a retrieval catheter constructed in accordance with the principles of the present invention.

Referring now to FIG. 6, a retrieval catheter 70 constructed in accordance with the principles of the present invention is described. Catheter 70 preferably includes tubular body 71, support wire 72, radiopaque marker 73 and opening 74. Body 71 and internal lumen 74 preferably are constructed to a have a diameter sufficient to accommodate an angioplasty catheter and a vascular filter such as described hereinabove with respect to FIGS. 1–3.

Body 71 preferably is fabricated from a thin biocompatible material, such as polyethylene, polypropylene, polyurethane, polyester, polyethylene terephthalate, nylon, polytetrafluoroethylene, polyimid, or Pebax®. Body 71 also is sufficiently stiff to be advanced along a guidewire through curved vasculature, and to retrieve a vascular filter, without buckling or kinking. Retrieval catheter 70 may be made radiopaque by using metal marker 73 or by constructing it of a radiopaque material such as a barium sulfate-infused ($BaSO_4$) polymer.

Figure 7A:
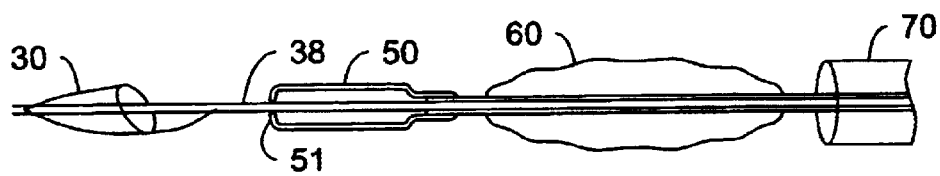
FIGS. 7A–7C are side sectional views depicting a method of retrieving the vascular filter of FIG. 3 using the retrieval catheter of FIG. 6 in conjunction with the apparatus of FIG. 4.

Retrieval catheter 70 may be mounted over a conventional interventional devices, such as an angioplasty catheter or stent delivery system, prior to inserting the interventional device into the patient's vasculature. For example, to mount retrieval catheter 70 on an angioplasty catheter, the distal end of the angioplasty catheter is inserted through distal end 75 of body 71, and the body then is retracted proximally on the angioplasty catheter until body 71 is disposed proximally of the balloon of the angioplasty catheter, as shown in FIG. 7A. Such backloading of the retrieval catheter is required because the inflation port of a typical angioplasty catheter precludes mounting retrieval catheter 70 from the proximal end of the angioplasty catheter.

Figure 7B:
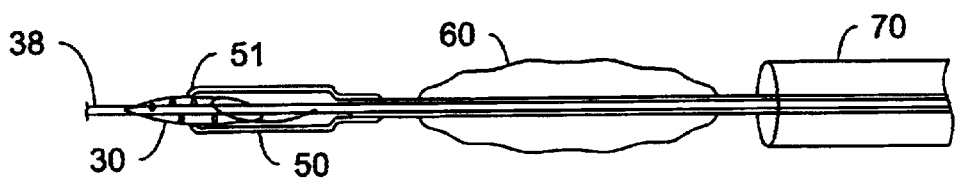
Figure 7C:
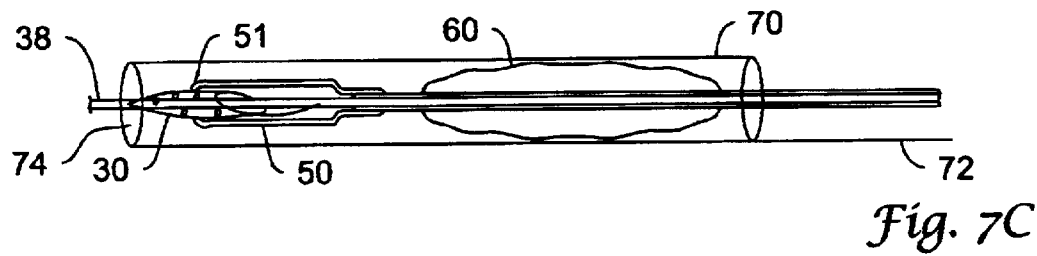

A first mode of using retrieval catheter 70 is now described with respect to FIGS. 7A–7C. In FIG. 7A, an initial step of a treatment procedure is depicted, wherein vascular filter 30 is disposed at a distal end of guidewire 38, just distal of adapter 50, interventional device 60, and retrieval catheter 70. Adapter 50 and retrieval catheter 70 are mounted to interventional device 60 prior to insertion along guidewire 38. After completion of the interventional procedure, the balloon of interventional device 60 is deflated, and the interventional device is urged in the distal direction to cause adapter 50 to contact with filter 30.

As shown in FIG. 7B, filter 30 may be received within the distal end 51 of adapter 50 when it is advanced further in the distal direction. In particular, adapter 50 is advanced by moving interventional device 60 along guidewire 38 so that it at least partially surrounds filter 30. Alternatively, adapter 50 may receive at least a portion of filter 30 by retracting guidewire 38 in the proximal direction while holding interventional device 60 stationary.

Next, as shown in FIG. 7C, retrieval catheter 70 is advanced distally so that filter 30 and adapter 50 are received within lumen 74 of retrieval catheter 70. In this manner it is possible to reduce the risk that the filter or adapter catches on other material, e.g., a stent, deployed within the patient's vessel during removal.

Figure 8A:
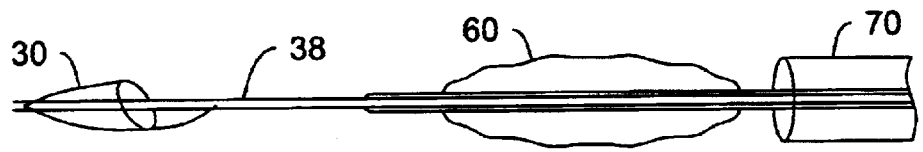
FIGS. 8A–8B are side sectional views depicting a method of retrieving the vascular filter of FIG. 3 using the retrieval catheter of FIG. 6 alone.
Figure 8B:
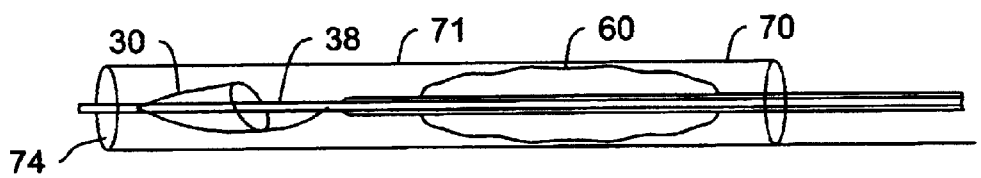

FIGS. 8A and 8B depict an alternative mode of using retrieval catheter 70 to retrieve a vascular filter without using adapter 50. In FIG. 8A, an initial step of a treatment procedure is depicted, wherein vascular filter 30 is disposed at a distal end of guidewire 38 followed by the balloon of an interventional device 60 and previously mounted retrieval catheter 70. After completing an interventional procedure, the balloon of interventional device 60 is deflated and advanced toward filter 30.

As shown in FIG. 8B, retrieval catheter 70 is then advanced distally so that the distal end of interventional device 60 and filter 30 are received in lumen 74 of the retrieval catheter. In this manner, the risk that emboli will escape from filter 30 is reduced. In addition, because body 71 of retrieval catheter 70 completely encloses filter 30, the risk that a portion of the filter sac could become entangled with a stent strut is also diminished. Alternatively, retrieval catheter 70 may be held stationary, and filter 30 retracted in the proximal direction into lumen 74.

Figure 9:
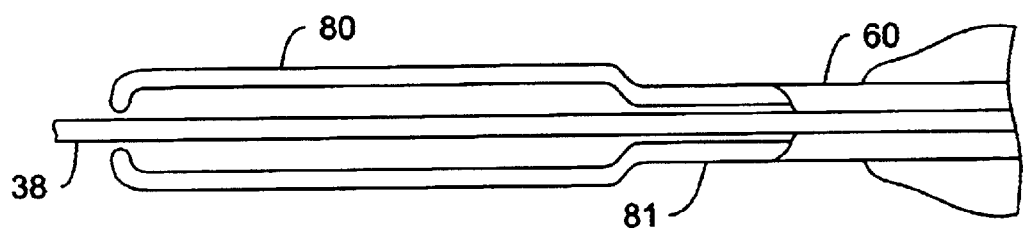
FIG. 9 is a side sectional view of an alternative method of using the apparatus of FIG. 4.

In FIG. 9, an alternative embodiment of a retrieval adapter constructed in accordance with the principles of the present invention is described. Adapter 80 is substantially similar to retrieval adapter 50 of FIG. 4, except that tapered proximal end 81 is configured to abut against the distal end of interventional device 60, rather than to couple together as shown in FIG. 5A.

Figure 10A:
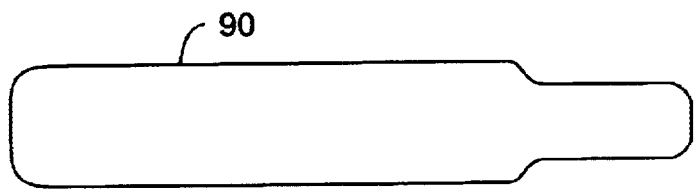
FIGS. 10A and 10B are side sectional views depicting an alternative embodiment of the apparatus of FIG. 4.
Figure 10B:
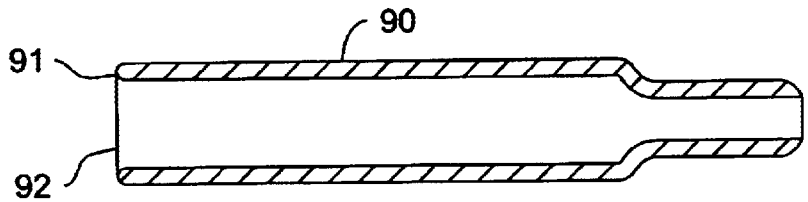

FIGS. 10A and 10B depict another alternative embodiment of the apparatus of the present invention. Adapter 90 is substantially similar to adapter 50 of FIG. 4, except that distal end 91 is not curved as in FIG. 4A, but instead includes a circular opening having a smooth, rounded edge. Lumen 92 preferably is of sufficient size to accommodate at least a portion of a deployed filter, thereby forming a close fit around at least a portion of the mouth of the filter.

Figure 11A:
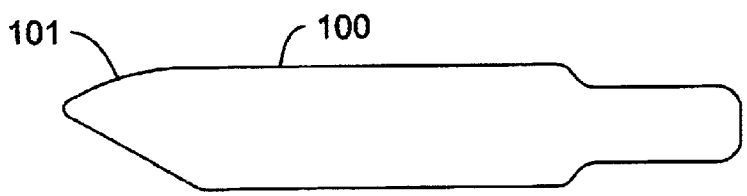
FIGS. 11A and 11B are side sectional views depicting another alternative embodiment of the apparatus of FIG. 4.
Figure 11B:
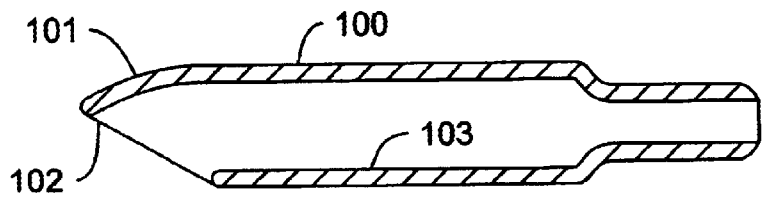

FIGS. 11A and 11B depict yet another alternative embodiment of the apparatus of the present invention. Adapter 100 is substantially similar to adapter 50 of FIG. 4, except that distal end 101 is not curved as in FIG. 4A, but instead includes an oblique opening 102 into lumen 103. Opening 102 preferably includes a smooth, rounded edge. As for the previously-described embodiments, lumen 103 preferably is of sufficient size to accommodate at least a portion of a deployed filter, and thus form a close fit around at least a portion of the mouth of the filter.

Each of adapters 50, 80, 90 and 100 may be coupled to (or disposed adjacent to) the distal end of an interventional catheter so that the adapter is delivered to a treatment site at the same time as the working element (i.e., balloon or stent) of the interventional device. Such concurrent delivery eliminates the steps of removing the interventional device from the patient's vessel and inserting a separate retrieval sheath to the treatment site along the guidewire.

Figure 12:
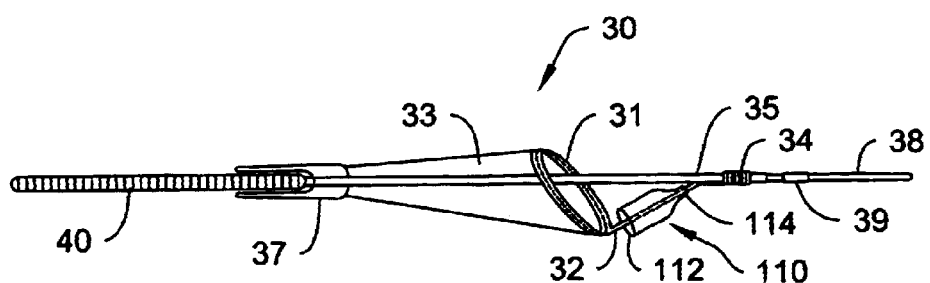
FIG. 12 is a side view of a further alternative embodiment of the apparatus of FIG. 4 incorporated into the vascular filter of FIG. 3.

Referring now to FIG. 12, a further alternative embodiment of the apparatus of the present invention is described. In this embodiment, retrieval adapter 110 is similar in construction to retrieval adapter 50 of FIG. 4, except that adapter 110 is pre-mounted on suspension strut 32 of vascular filter 30. In particular, adapter 110 includes lumen 112 and tapered proximal region 114.

In operation, an interventional device may be advanced along guidewire 38 until it abuts proximal end 114 of adapter 110, pushing the adapter distally along suspension strut 32 towards support hoop 31 of filter 30, until support hoop 31 is received within lumen 112. The extent to which adapter 110 receives support hoop 31 may of course be determined by the length of adapter 110. Alternatively, adapter 110 may collapse and retrieve vascular filter 30 by retracting guidewire 38 such that filter 30 is retracted proximally towards the adapter while holding the interventional device stationary.

Figure 13A:
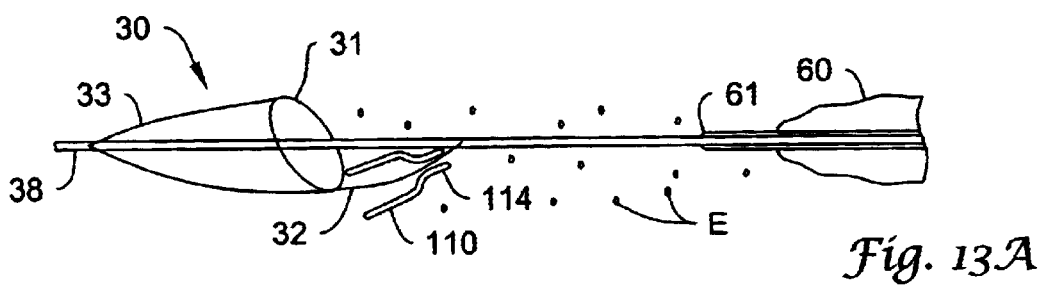
FIGS. 13A–13C are side sectional views depicting a method of using apparatus of FIG. 12.
Figure 13B:
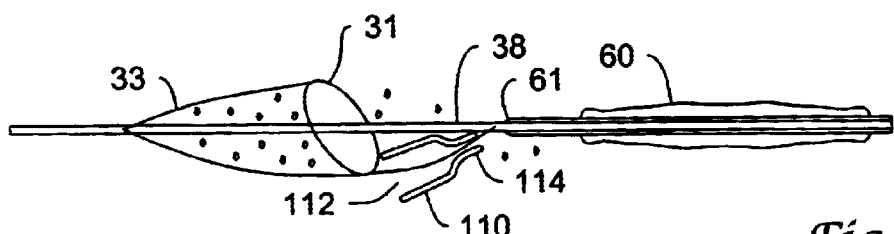
Figure 13C:
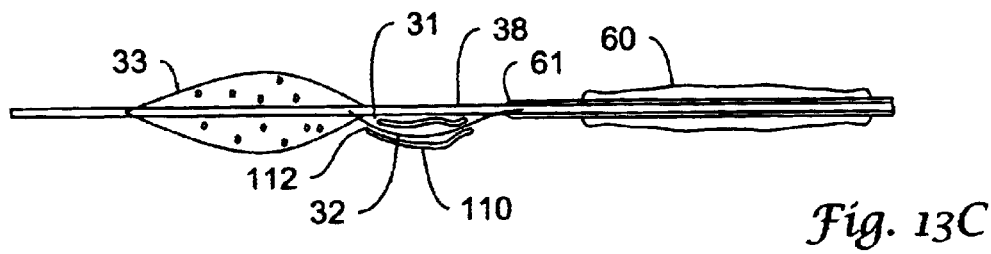

FIGS. 13A–13C depict one method of using the apparatus of FIG. 12. In FIG. 13A, during an initial step of an interventional procedure, filter 30 with pre-mounted retrieval adapter 110 is deployed in a vessel (not shown). A conventional interventional device 60, illustratively an angioplasty catheter, is then advanced along guidewire 38 until distal end 61 of the interventional device is disposed just proximal of, or in contact with, the proximal end of the adapter. Preferably, the adapter is positioned sufficiently far from the proximal end of the vascular filter that small longitudinal movements of interventional device 60 attendant upon use of that device do not cause distal end 61 to impinge against tapered proximal region 114 of adapter 110. It will of course be recognized that in some applications, e.g., where the vessel is short, some contact between the adapter and vascular filter can be accommodated.

Interventional device 60 then is used to perform the desired diagnostic or therapeutic treatment, during which emboli E may become dislodged from the vessel wall. Those emboli travel with antegrade blood flow and are captured in blood permeable sac 33 of filter 30. After completion of this procedure, the balloon of the interventional device is deflated and the interventional device is advanced along guidewire 38 in the distal direction to bring distal end 61 of the interventional device into abutment with tapered proximal region 114 of adapter 110, as shown in FIG. 13B.

With respect to FIG. 13C, continued advancement of interventional device 60 in the distal direction causes support hoop 31 of filter 30 to at least partially enter lumen 112 of adapter 110, thereby causing the support hoop to close and closing the mouth of filter sac 33. Alternatively, adapter 110 may be caused to at least partially surround support hoop 31 by retracting guidewire 38 proximally while holding interventional device 60 stationary.

The degree to which vascular filter 30 is captured in adapter 110 depends on the length of lumen 112 within adapter 110 and also is limited by the length of the support hoop when folded over guidewire 38. Specifically, vascular filter 30 may be received within lumen 112 of adapter 110 until the point on support hoop 31 opposite to the connection to suspension strut 32 is urged against guidewire 38.

Because closing the vascular filter may prevent the vascular device from being re-deployed, it may be desirable to prevent the inadvertent closing of vascular filter 30. Such inadvertent closing may be prevented by using a safety system deployed along guidewire 38, as shown in the embodiment of FIG. 14.

Figure 14:
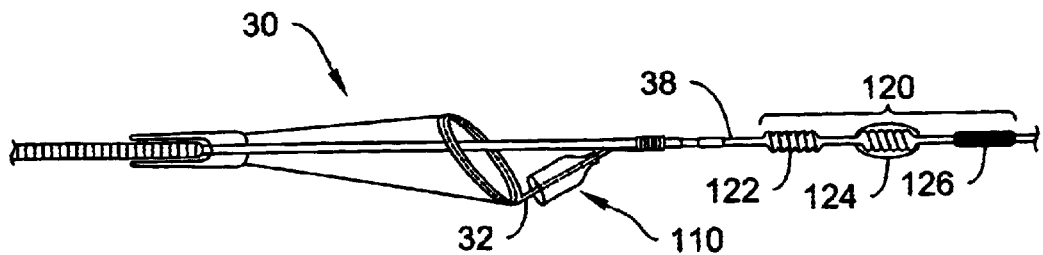
FIG. 14 is a side view of yet another alternative embodiment of the apparatus of FIG. 4 incorporated into the vascular filter of FIG. 3.

In FIG. 14, vascular filter 30 is disposed on guidewire 38 and includes adapter 110 disposed on suspension strut 32 in the same manner as depicted in FIG. 12. In accordance with this aspect of the present invention, guidewire 38 includes safety system 120 comprising screw 122, nut 124 and stop 126. Preferably, these components are constructed of a high strength plastic or metal alloy, such as stainless steel.

Safety system 120 is intended to prevent an interventional device, such as a balloon catheter or stent delivery system, from accidentally closing vascular filter 30. Screw 122 and stop 126 preferably are fixed on guidewire 38, while nut 124 is configured to move freely along guidewire 38 between screw 122 and stop 126. Stop 126 restricts movement of nut 124 in the proximal direction, while screw 122 selectively restricts movement of nut 124 in the distal direction.

Nut 124 may be advanced past screw 122 by rotating guidewire 38 such that the threads of the screw mesh with the threads of the nut, thus advancing the nut over and past the screw until the nut is disposed distally of the screw, i.e., between filter 30 and screw 122. When nut 124 is disposed between screw 122 and stop 126, it prevents the interventional device from advancing distally toward adapter 110 until guidewire 38 is intentionally rotated. Once the intended diagnostic or therapeutic procedure is completed, however, nut 124 is moved to a position between filter 30 and screw 122 by rotating guidewire 38, and then the interventional device may be advanced distally over stop 126 and screw 122 to urge nut 124 into engagement with adapter 110, thereby closing filter 30.

Figure 15A:
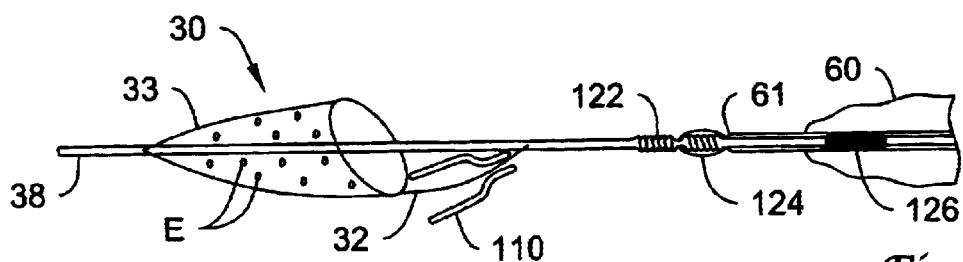
FIGS. 15A–15C are side sectional views depicting a method of using apparatus of FIG. 14.
Figure 15B:
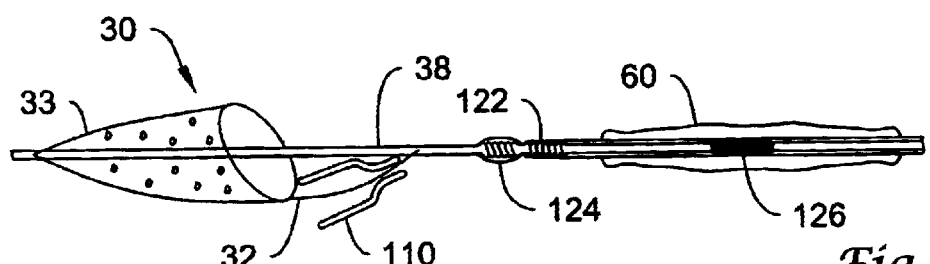
Figure 15C:
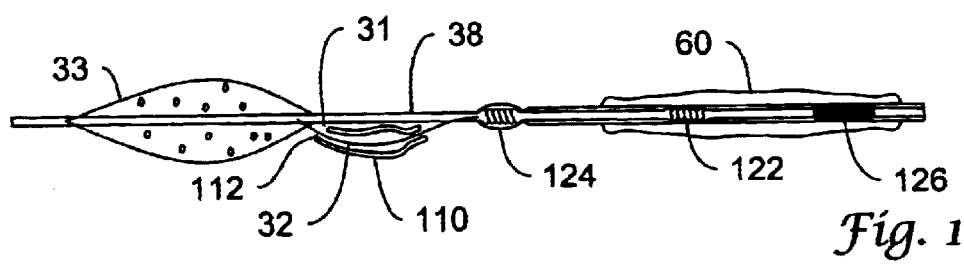

FIGS. 15A–15C depict a method of using the apparatus of FIG. 14. In FIG. 15A, during an initial step of an interventional procedure, filter 30 is deployed in a vessel (not shown) and includes adapter 110 disposed on suspension strut 32, and safety system 120 disposed on guidewire 38. A conventional interventional device 60, illustratively an angioplasty catheter, is advanced along guidewire 38 and then used to effect a desired diagnostic or therapeutic treatment, during which emboli E may become dislodged from the vessel wall. Those emboli travel with antegrade blood flow and are captured in blood permeable sac 33 of filter 30.

After completion of this procedure, the balloon of the interventional device is deflated and the interventional device is advanced along guidewire 38 in the distal direction and over stop 126 until distal end 61 of the interventional device contacts nut 124. The distal end of interventional device 61 may push nut 124 until it is in direct contact with screw 122.

Next, as shown in FIG. 15B, nut 124 is advanced over and past screw 122 by rotating guidewire 38 so that the threads of nut 124 mesh with and advance over the threads of screw 122. Interventional device 60 is then advanced distally over screw 122 to urge nut 124 into contact with the proximal end of adapter 110. As shown in FIG. 15C, further advancement of interventional device 60 in the distal direction causes nut 124 to urge adapter 110 distally, whereby support hoop 31 is received at least partially within lumen 112 of the adapter. In this manner filter 30 may be collapsed for retrieval with little effort and without an additional equipment exchange or additional retrieval sheath. As for the previous embodiments, adapter 110 alternatively may be caused to at least partially surround support hoop 31 by retracting guidewire 38 proximally while holding interventional device 60 stationary.

Although the present invention is illustratively described in the context of interventional devices such as angioplasty catheters and stent delivery systems, the apparatus of the present invention advantageously may be employed with atherectomy catheters, embolectomy catheters, vascular mapping catheters or any other suitable diagnostic or therapeutic interventional device, if desired.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for use in conjunction with an interventional device in retrieving a vascular filter disposed on a guidewire from a vessel, the apparatus comprising:
    a retrieval adapter having a proximal end, a distal end and a lumen, the retrieval adapter configured to be disposed on a distal region of the guidewire so that the proximal end engages a distal end of the interventional device, the retrieval adapter configured to receive at least a portion of the vascular filter within the lumen during retrieval of the vascular filter from the vessel.

2. The apparatus of claim 1 wherein the retrieval adapter comprises a biocompatible material.

3. The apparatus of claim 1 wherein the retrieval adapter comprises a radiopaque material.

4. The apparatus of claim 3 wherein the radiopaque material comprises a radiopaque coil embedded in the retrieval adapter.

5. The apparatus of claim 1 wherein the proximal end of the retrieval adapter is tapered to facilitate engagement with a distal end of the interventional device.

6. The apparatus of claim 5 wherein the retrieval adapter is mounted on the distal end of the interventional device.

7. The apparatus of claim 5 wherein the proximal end of the retrieval adapter abuts against the distal end of the interventional device.

8. The apparatus of claim 1 wherein the distal end of the retrieval adapter includes at least one slit.

9. The apparatus of claim 1 wherein the distal end of the retrieval adapter is perforated.

10. The apparatus of claim 1 wherein the retrieval adapter has a length less than about 50 mm.

11. A system for retrieving a vascular filter comprising:
    a guidewire having a distal end;
    a vascular filter disposed on the guidewire adjacent the distal end of the guidewire;
    an interventional device having a distal end and a lumen extending therethrough the interventional device disposed on the guidewire proximally of the vascular filter; and
    a retrieval adapter slidingly disposed on the guidewire and interposed between the vascular filter and the distal end of the interventional device.

12. The system of claim 11 wherein the retrieval adapter includes a lumen adapted to receive at least a portion of the vascular filter.

13. The system of claim 11 wherein the retrieval adapter comprises a biocompatible material.

14. The system of claim 11 wherein the retrieval adapter comprises a radiopaque material.

15. The system of claim 14 wherein the radiopaque material comprises a radiopaque coil embedded in the retrieval adapter.

16. The system of claim 11 wherein the retrieval adapter further comprises a proximal region tapered to facilitate engagement with the distal end of the interventional device.

17. The system of claim 16 wherein the retrieval adapter is configured to be mounted on the distal end of the interventional device.

18. The system of claim 11 wherein a distal end of the retrieval adapter includes at least one slit.

19. The system of claim 11 wherein a distal end of the retrieval adapter is perforated.

20. The system of claim 11 wherein the retrieval adapter has a length of less than about 50 mm.

21. A system for retrieving a vascular filter comprising:

a guidewire having a distal end;

a vascular filter disposed on the guidewire adjacent the distal end of the guidewire, the vascular filter comprising a suspension strut coupled to the guidewire, a support hoop coupled to the suspension strut, and a blood permeable sac coupled to the support hoop;

an interventional device having a distal end and a lumen extending therethrough the interventional device disposed on the guidewire proximally of the vascular filter; and a retrieval adapter slidingly disposed on the suspension strut.

22. The system of claim 21 wherein the retrieval adapter includes a lumen adapted to receive at least a portion of the vascular filter.

23. The system of claim 21 wherein the retrieval adapter comprises a biocompatible material.

24. The system of claim 21 wherein the retrieval adapter comprises a radiopaque material.

25. The system of claim 21 wherein a distal end of the retrieval adapter is radially expandable.

26. The system of claim 21 further comprising a safety device that inhibits inadvertent closing of the vascular filter.

27. A method of retrieving a vascular filter comprising:

providing a guidewire, a vascular filter, an interventional device and a retrieval adapter;

deploying the vascular filter on the guidewire distal to a treatment site;

disposing a retrieval adapter on the guidewire in engagement with a distal end of the interventional device;

advancing the retrieval adapter and interventional device along the guidewire to the treatment site;

performing a diagnostic or therapeutic procedure at the treatment site using the interventional device; and upon completion of the diagnostic or therapeutic procedure, advancing the interventional device distally along the guidewire so that the retrieval adapter captures the vascular filter.

28. The method of claim 27 wherein advancing the interventional device distally along the guidewire cause the vascular filter to be received at least partially within a lumen of the retrieval adapter.

29. A method of retrieving a vascular filter comprising:

providing a guidewire, a vascular filter including a retrieval adapter and an interventional device;

deploying the vascular filter and retrieval adapter on the guidewire distal to a treatment site;

advancing the interventional device along the guidewire to the treatment site;

performing a diagnostic or therapeutic procedure at the treatment site using the interventional device;

upon completion of the diagnostic or therapeutic procedure, advancing the interventional device distal along the guidewire so that the interventional device abuts against the retrieval adapter; and advancing the interventional device further distally along the guidewire so that the interventional device causes the retrieval adapter to capture the vascular filter.

30. The method of claim 29 wherein advancing the interventional device distally along the guidewire cause the vascular filter to be receive at least partially within a lumen of the retrieval adapter.

* * * * *